United States Patent [19]

Brighton

[11] Patent Number: 4,467,809
[45] Date of Patent: Aug. 28, 1984

[54] METHOD FOR NON-INVASIVE ELECTRICAL STIMULATION OF EPIPHYSEAL PLATE GROWTH

[75] Inventor: Carl T. Brighton, Malvern, Pa.

[73] Assignee: Biolectron, Inc., Hackensack, N.J.

[21] Appl. No.: 419,433

[22] Filed: Sep. 17, 1982

[51] Int. Cl.³ ............................................. A61N 1/06
[52] U.S. Cl. ............................................. 128/419 F
[58] Field of Search ............ 128/419 R, 419 F, 82.1, 128/422

[56] References Cited

U.S. PATENT DOCUMENTS

| | | | |
|---|---|---|---|
| 3,783,880 | 1/1974 | Kraus | 128/82.1 |
| 3,893,462 | 7/1975 | Manning | 128/419 F |
| 3,902,502 | 9/1975 | Liss et al. | 128/422 |
| 3,989,050 | 11/1976 | Buchalter | 128/419 R |
| 4,055,190 | 10/1977 | Tany | 128/422 |
| 4,093,975 | 6/1978 | Roberts | 128/422 |
| 4,154,240 | 5/1979 | Ikuno et al. | 128/422 |
| 4,237,898 | 12/1980 | Whalley | 128/422 |
| 4,249,537 | 2/1981 | Lee et al. | 128/422 |
| 4,315,503 | 2/1982 | Ryaby et al. | 128/82.1 |

OTHER PUBLICATIONS

Lavine et al. "The Influence of Electric Current on Bone Regeneration in Vivo" *ACTA Ortho-p Scandinav* vol. 12 pp. 305-314 1971.

Mooar, P. A., Brighton, C. T. et al.; Article entitled "Stimulation of In Vitro Epiphyseal Plate Growth by a Time Varying Electric Field".

Brighton, C. T., Wisneski, R. J.; Article entitled "Electrical Enhancement of Growth Plate DNA Synthesis In Vitro With Low Voltage Capacitive Coupling".

*Primary Examiner*—William E. Kamm
*Assistant Examiner*—Mitchell J. Shein
*Attorney, Agent, or Firm*—Brumbaugh, Graves, Donohue & Raymond

[57] ABSTRACT

Epiphyseal growth plate stimulation in the bone of a living body is achieved by applying electrodes non-invasively to a body and supplying to said electrodes an AC signal in the range of about 2.5 to 15 volts peak-to-peak at a frequency of about 20-100 KHz.

9 Claims, 7 Drawing Figures

METHOD FOR NON-INVASIVE ELECTRICAL STIMULATION OF EPIPHYSEAL PLATE GROWTH

TECHNICAL FIELD

This invention relates to a non-invasive method for stimulating growth in the epiphyseal plate in the bone of a living body by electrical stimulation.

BACKGROUND OF THE INVENTION

Bone formation arises by a transformation of connective tissue, and may be preceded either by the laying down of cartilage, or by direct transformation of fibrous tissue. In bones which have been preformed in cartilage, a portion of the cartilage persists throughout the period of growth as a cartilage plate. This cartilage continues to grow, and is constantly replaced by bone, resulting in lengthwise bone growth. The cartilage with its surrounding tissues, also contributing to growth, has been called the growth apparatus. In long bones the growth apparatus is at the epiphyses or ends of the bones.

The length of the bone is controlled by the rate of growth of the epiphyseal line, which is the small cartilage plate at the end of the bone. Various stimuli have been implemented in trying to stimulate bone growth at the epiphyseal line. These stimuli have included periosteal irritation, radiation, medullary plugging, creation of an arteriovenous fistula, sympathetic denervation, heat, insertion of foreign objects into the epiphyses/metaphyses, and electricity. The methods of electrical stimulation have included electrolysis, i.e. the use of implanted dissimilar metals to produce a small current, direct current, electromagnetic fields and electric fields, both static and dynamic.

Efforts using electrolysis electrical stimulation have included inserting dissimilar metal strips into the metaphyses close to the growth plate on mongrel dogs, and creating a current of 10–20 microamperes between the two strips. However any positive results obtained were insignificant. Further work using bimetallic strips resulted in the stimulation of longitudinal growth, but the stimulus was unpredictable.

Other work has included that of Bassett who in 1974 showed that a capacitively coupled asymmetric electrostatic field increased the repair rate of fibular osteotomies in a rabbit. Watson in 1975 reported an increase in the length of embryonic chick tibiae grown in vitro in a pulsed square wave 1000 V/cm electric field. However, Watson obtained no positive results with a static field. Louis Norton in 1974 reported increased metabolic activity in the metatarsus bones of newborn chicks in response to a 5 Hz unidirectional signal ranging from 163 V to 490 V applied between two electrode capacitive plates. In 1977, Norton reported an increase in cAMP in response to a 900 V 5 Hz unidirectional signal, which increase tailed off at voltages above 1250 V. In 1976 Rodan and Norton demonstrated an enhanced incorporation of 3H-thymidine, in chondrocyte cultures, in response to a 1166 V/cm signal oscillating at 5 Hz. Similar results were reported by Norton working with membranous bone from rat calvaria in 1977.

In 1981, I reported electrical enhancement of growth plate DNA synthesis in vitro with low voltage capacitive coupling. In this experiment, costochondral junctions were excised from rats and were anchored to tightly sealed Petri dishes and grown in tissue culture medium. The Petri dishes were stimulated for 24 hours between intimately contacting, parallel, stainless steel plates using a stimulation signal of 10 V peak-to-peak, at a frequency of 60 KHz, with and without 50% amplitude modulation. Analysis of the samples indicated increased DNA synthesis of the experimental (stimulated) group relative to the control (unstimulated) group. However, the experiments were limited to in vitro specimens stimulated in Petri dishes.

In early 1982, I reported stimulation of in vitro epiphyseal plate growth by a time varying electric field using stimulation signals of 5–80 V peak-to-peak, frequencies between 30 and 120 KHz, and 0%, 50% and 100% modulation. Stimulatory effects of increased DNA synthesis was noted particularly over the range of 5–50 volts peak-to-peak and over a frequency range of 30–60 KHz. Again, this experiment was limited to in vitro specimens of costochondral junctions of rats stimulated in Petri dishes. While increased DNA synthesis was observed in this and the former experiment, both experiments were limited to in vitro specimens. Therefore, it was still not known whether certain stimulation signals would result in longitudinal bone growth at the epiphyseal growth plate in vivo, (i.e. in living bodies).

SUMMARY OF THE INVENTION

In accordance with the present invention, bone growth at the epiphyseal growth plate in a living body is promoted by non-invasively applying electrodes to a subject's body in the vicinity of the epiphyseal growth plate of a bone and supplying to the electrodes an AC stimulation signal having a frequency of about 20–100 KHz. By applying the signal in this manner, intermittently or continuously for a sufficient period of time, an increase in bone growth is effected as compared with bone growth that would occur naturally.

For better understanding of the above and other features and advantages of the invention, reference is made to the following detailed description of a preferred procedure according to the invention taken in conjunction with the following drawings.

DESCRIPTION OF THE PREFERRED EMBODIMENT

Figure 1:
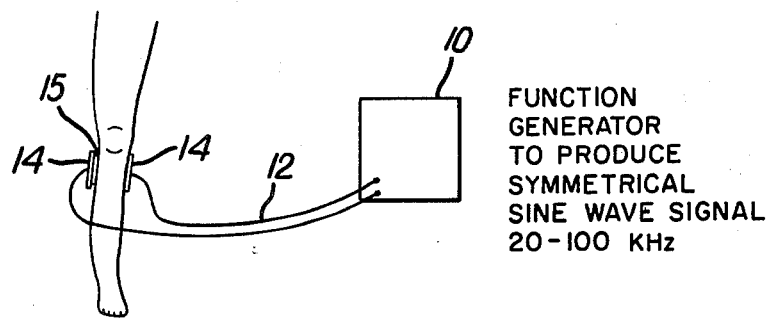
FIG. 1 is a simplified schematic representation of a signal generating system and electrical leads for noninvasively providing a signal to a living subject in the vicinity of the epiphyseal growth plate of a bone according to the invention.

While this invention may be practiced in many different forms, there is shown in the drawings and will herein be described in detail one specific method, with the understanding that the present disclosure is to be considered as an exemplification of the principles of the invention and is not intended to limit the invention to the precise method illustrated.

FIG. 1 shows a signal frequency generator 10 which generates an AC stimulation signal having a frequency within the range of about 20–100 KHz. The waveform of the AC stimulation signal is preferably an unmodulated symmetrical sinewave having a peak-to-peak amplitude within the range of about 2.5–15 volts peak-to-peak and more preferably within the range of about 5–10 volts peak-to-peak. The frequency generator 10 can be a Wave Tech Model 148 Function Generator. The stimulation signal is supplied by the wires 12 to a pair of stimulation electrodes 14 non-invasively applied to the skin of a living body at positions in the vicinity of the epiphyseal growth plate of a bone. In order to achieve good electrical contact, the skin of the subject can be shaved initially and periodically to remove any hair, and a conductive jelly such as K-Y lubricating jelly (Johnson & Johnson) can be applied to the skin before the electrodes are non-invasively applied or reapplied to the skin.

It should be understood that the electrodes should preferably be positioned relatively close to the epiphyseal growth plate of a bone. However, the electrodes may be applied at locations remote from the epiphyseal growth plate, where that proves necessary or desirable because of the particular bone selected to be stimulated.

While the electrodes 14 are preferably bare metal placed in direct contact with the skin after the application of K-Y gel, one or both of the electrodes may be coated with dielectric material such as Mylar film 15.

EXAMPLE

Efficacy of the procedure according to the invention has been established in the following clinical experiment.

A total of 80 seven-week old New Zealand white rabbits were selected for uniform growth and were distributed into four equal groups with each group having 10 control (unstimulated) animals and 10 experimental (stimulated) animals. The right proximal medial and lateral tibial epiphyses of all of the rabbits were shaved, and then a pair of electrodes 14 in the form of 1.8 sq. cm. stainless steel plates was placed in parallel over the medial and lateral right tibial shaved areas of each rabbit. The electrodes were held in place by a plastic jig and moleskin wrap, which allowed for relatively normal weight bearing and free range of motion at the knee. The lead wires to the electrodes 14 were Teflon coated and encased in springs to prevent the animals from chewing the wires, and were connected to a rotating electrical connector at the top of the cage which allowed the wires to be untangled without disconnecting the wires, while also allowing the animal ample scope of movement.

At the onset of the experiment (day 0) all animals received 3 mg/kg of intravenous oxytetracycline via the ear vein. Oxytetracycline has been found to have a strong affinity for mineralizing cartilage and bone tissue, and accumulates in skeletal locations where new bone matrix or hyaline cartilage is mineralizing. Since a rapid intraveneous pulse is given, an instantaneous fluorescent marker is established at the epiphyseal-metaphyseal border to provide a label parallel to the border. As bone increases in length the label remains incorporated in the metaphysis. When examined under ultraviolet light, the marker or label fluoresces green-yellow and is thus distinct from surrounding structures, and provides a means of measuring longitudinal bone growth.

All animals received a second injection of oxytetracycline 2 days after the first injection (day 2). Commencing at the time of the second injection, the animals were reshaved, K-Y lubricating jelley was applied to the skin and electrodes 14 were reapplied to the right tibial area to insure good electrical contact, and the experimental animals in each group were stimulated with a continuous low voltage 60 KHz symmetrical sine wave signal from the generator 10 for two days (from day 2 to day 4).

The signals were provided by a number of generators 10, with each generator servicing five animals. The amplitude of the signal for group 1 was 2.5 volts peak-to-peak, for group 2 it was 5 volts, for group 3 it was 10 volts, and for group 4 it was 20 volts. The signal was monitored every eight hours with a Techtronics T922 Oscilloscope.

The currents passing through the electrodes 14 were calculated from the voltage drop across a 100 ohm resistor placed in series with the electrodes as measured by a Hewlett Packard Digital Multimeter. The rms current across the pairs of electrodes 14 for the stimulated animals in group 1 was 1.24 mamps $\pm 0.32$ (range 0.54–2.44), 1.10 mamps $\pm 0.42$ (range 0.18–3.04) for the animals in group 2, 1.53 mamps $\pm 0.64$ (range 0.08–8.36) for the animals in group 3 and approximately 7 mamps for the animals in group 4. The control animals received no stimulation during this period.

The jigs used to hold the electrodes in place caused pedal edema to develop in some animals, and this condition was graded on a scale of 0–3 (0=absent, 1=mild, 2=pitting and 3=weeping) on both days 2 and 4. The animals were weighed on days 0 and 4.

On day 4, 96 hours after the first injection, all animals were sacrificed and the tibiae were dissected and stored in 40% ethyl alcohol for a maximum of 16 hours. The midlateral proximal tibiae were then longitudinally cut into sagittal or planar section slices approximately 100 microns in thickness using a Buehler "Isomet" low speed diamond saw, exercising care to obtain sections perpendicular to the growth plate. A slab of proximal tibia was then ground down to 10 microns on a Buehler Grinder No. 320. The specimens were kept water wet during the entire procedure. Each specimen was then dehydrated in ethyl alcohol and permanently mounted on a microscopic slide with Eukitt's Mounting Media and kept out of direct light to minimize fading of the tetracycline label.

Longitudinal growth was quantified using microscopic epifluoresence and a Zeiss MOP-3 measurement system. All specimens were read blindly. The longitudinal distance between the first and the second oxytetracycline line (indicating growth during the unstimulated period, days 0–2) and the second oxytetracycline line and the bone-cartilage junction (indicating growth during the stimulated period, days 2–4) was measured in both the control and experimental animals under 16×magnification.

Each distance was calculated from the mean of twelve separate measurements taken at equal intervals across the growth plate of each specimen. An eyepiece grid was used to ensure uniform specimen alignment and equal measurement intervals. The precision of the system was tested beforehand by performing ten consecutive measurements on the same specimen.

DATA ANALYSIS

Two basic analyses of the data were made. In the first analysis the growth in the stimulated (experimental) animals was compared to growth in the unstimulated (control) animals for the stimulation period (days 2–4) only. This analysis was done for all four groups. In the second analysis, only the data for the stimulated animals in group 3 was analyzed. In this analysis, the growth in stimulated animals during the stimulation period (days 2–4) was compared to the growth of the same animal during their unstimulated period (days 0–2).

1. First Analysis

For the first analysis, the longitudinal proximal tibial growth data was tabulated, and ratios of right-to-left (i.e. R/L) growth for this 2 day stimulation period (days 2–4) were calculated for both the stimulated (experimental) animals and unstimulated (control) animals, (see Tables I, II, III, and IV). While 10 control and 10 experimental animals were initially present in each group, in some cases 1 or 2 animals were eliminated from the table for various reasons.

As mentioned, only the right tibia of each experimental animal was stimulated. By measuring both the right and left tibiae for all animals, and then by calculating a ratio of right/left (R/L) for the tibiae of each animal, control for any growth or disease mechanisms that might be naturally occurring in the animal was obtained.

Figure 2:
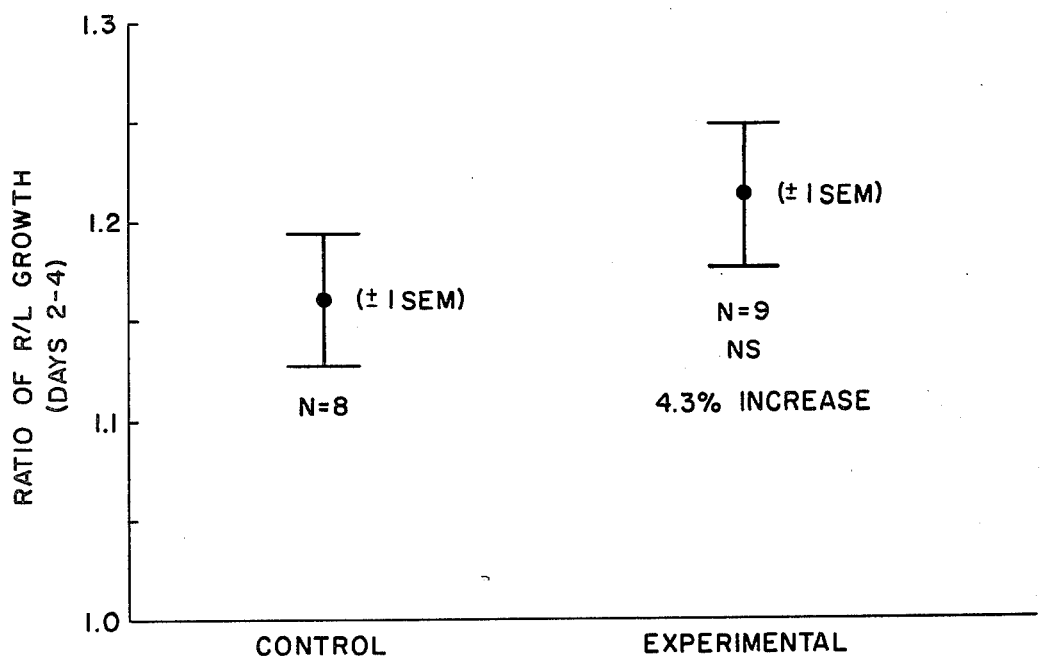
FIGS. 2–5 inclusive, are graphs illustrating typical quantified results of in vivo growth plate stimulation using signals of 2.5, 5.0, 10.0 and 20 volts peak-to-peak respectively, in the system of FIG. 1.

As seen in Table I and FIG. 2, the group 1 animals (2.5 volts stimulation) experienced a 4.3% increase in length from 1.16 average ratio R/L to 1.21 average ratio R/L. However, under statistical analysis using the "group-t" test, the results were not statistically significant. The correlation coefficients for current, weight gain and edema ($r = 0.27$, 0.14 and 0.07 respectively) revealed no statistical significance when compared to growth.

Figure 3:
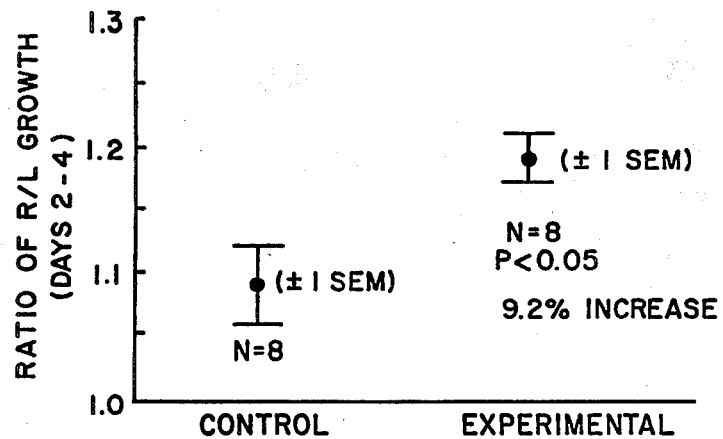

For group 2 animals (5.0 volts stimulation) in Table II, a 9.2% increase in length was obtained, from 1.09 average ratio R/L to 1.19 average ratio R/L, (see FIG. 3). This result is statistically significant ($p\ 0.05$) under group t-test analysis. Again, no significant linear correlation appears to exist between longitudinal growth and either current, weight change or edema (with correlation of $r = 0.28$, 043 and 0.10 respectively).

Figure 4:
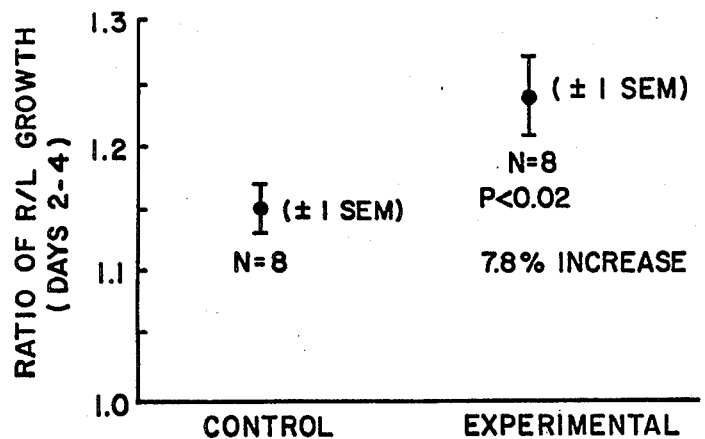

Table III and FIG. 4 illustrate that the group 3 animals (10.0 volts stimulation) experienced an 7.8% increase in bone length, from 1.15 average ratio R/L to 1.24 average ratio R/L, which was also statistically significant ($p\ 0.02$) under group t-test anaylsis. Again, there was no significant correlation between growth and current, weight change or edema (with correlations of $r = 0.23$, 0.06 and 0.23 respectively).

TABLE I

Longitudinal Proximal Tibial Growth with
Stimulation of 2.5 Volts P-P
(50 units = 1 mm)

| | Control | | Experimental | |
|---|---|---|---|---|
| | R | L | R | L |
| | 33.02 | 29.80 | 32.76 | 32.75 |
| | 33.82 | 26.68 | 30.03 | 27.67 |
| | 32.89 | 30.65 | 31.80 | 25.81 |
| | 35.33 | 29.32 | 37.36 | 30.73 |
| | 28.17 | 26.38 | 32.39 | 27.28 |
| | 34.28 | 33.10 | 32.79 | 26.68 |
| | 35.48 | 29.41 | 39.92 | 29.20 |
| | 32.51 | 25.43 | 42.92 | 32.93 |

TABLE I-continued

Longitudinal Proximal Tibial Growth with
Stimulation of 2.5 Volts P-P
(50 units = 1 mm)

| | | | 33.35 | 25.97 |
|---|---|---|---|---|
| ($\bar{x}$) | 33.19 | 28.85 | 34.81 | 28.78 |
| (SD) | 2.3 | 2.54 | 4.28 | 2.77 |
| (SE) | 0.81 | 0.90 | 1.43 | 0.92 |
| | R/L | | R/L | |
| | 1.11 | | 1.00 | |
| | 1.27 | | 1.09 | |
| | 1.07 | | 1.23 | |
| | 1.21 | | 1.22 | |
| | 1.07 | | 1.19 | |
| | 1.04 | | 1.23 | |
| | 1.21 | | 1.37 | |
| | 1.28 | | 1.30 | |
| | | | 1.28 | |
| ($\bar{x}$) | 1.16 | | 1.21 | |
| (SD) | 0.10 | | 0.11 | |
| (SE) | 0.03 | | 0.04 | |

4.3% ↑
NS

TABLE II

Longitudinal Proximal Tibial Growth with
Stimulation of 5 Volts P-P
(50 units = 1 mm)

| | Control | | Experimental | |
|---|---|---|---|---|
| | R | L | R | L |
| | 37.87 | 34.16 | 36.23 | 27.78 |
| | 37.00 | 35.88 | 41.12 | 32.90 |
| | 38.67 | 34.71 | 23.54 | 19.58 |
| | 29.33 | 32.11 | 32.35 | 29.93 |
| | 27.21 | 23.48 | 34.28 | 30.52 |
| | 32.32 | 27.83 | 30.42 | 26.65 |
| | 36.93 | 32.73 | 27.73 | 23.99 |
| | 27.38 | 24.88 | 33.28 | 26.76 |
| | | | 38.85 | 32.86 |
| ($\bar{x}$) | 33.34 | 30.72 | 33.09 | 27.89 |
| (SD) | 4.86 | 4.71 | 5.44 | 4.30 |
| (SE) | 1.72 | 1.66 | 1.81 | 1.43 |
| | R/L | | R/L | |
| | 1.11 | | 1.30 | |
| | 1.03 | | 1.25 | |
| | 1.11 | | 1.20 | |
| | 0.91 | | 1.08 | |
| | 1.16 | | 1.12 | |
| | 1.16 | | 1.14 | |
| | 1.13 | | 1.16 | |
| | 1.10 | | 1.24 | |
| | | | 1.18 | |
| ($\bar{x}$) | 1.09 | | 1.19 | |
| (SD) | 0.08 | | 0.07 | |
| (SE) | 0.03 | | 0.02 | |

9.2% ↑
$P < 0.05$

TABLE III

Longitudinal Proximal Tibial Growth with
Stimulation of 10 Volts P-P
(50 units = 1 mm)

| | Control | | Experimental | |
|---|---|---|---|---|
| | R | L | R | L |
| | 36.16 | 31.73 | 43.90 | 34.02 |
| | 32.85 | 29.68 | 34.75 | 26.52 |
| | 36.91 | 31.54 | 29.18 | 24.69 |
| | 37.34 | 32.97 | 42.30 | 31.18 |
| | 41.42 | 34.15 | 33.74 | 29.00 |
| | 33.14 | 26.63 | 41.63 | 36.24 |
| | 36.03 | 33.72 | 43.38 | 34.96 |
| | 36.60 | 33.13 | 37.34 | 30.16 |
| ($\bar{x}$) | 36.31 | 31.69 | 38.28 | 30.85 |

TABLE III-continued

Longitudinal Proximal Tibial Growth with
Stimulation of 10 Volts P-P
(50 units = 1 mm)

| | | | | |
|---|---|---|---|---|
| (SD) | 2.67 | 2.49 | 5.37 | 4.08 |
| (SE) | 0.94 | 0.88 | 1.90 | 1.44 |

| | R/L | | R/L |
|---|---|---|---|
| | 1.14 | | 1.29 |
| | 1.11 | | 1.31 |
| | 1.17 | | 1.18 |
| | 1.13 | | 1.36 |
| | 1.21 | | 1.16 |
| | 1.25 | | 1.15 |
| | 1.07 | | 1.24 |
| | 1.11 | | 1.24 |
| ($\bar{x}$) | 1.15 | | 1.24 |
| (SD) | 0.06 | | 0.08 |
| (SE) | 0.02 | | 0.03 |
| | | 7.8% ↑ | |
| | | $p<0.02$ | |

TABLE IV

Longitudinal Proximal Tibial Growth with
Stimulation of 20 Volts P-P
(50 units = 1 mm)

| | Control | | Experimental | |
|---|---|---|---|---|
| | L | R | L | R |
| | 30.30 | 31.43 | 28.06 | 30.43 |
| | 25.68 | 33.25 | 32.63 | 30.55 |
| | 27.43 | 32.42 | 35.53 | 37.36 |
| | 27.80 | 32.25 | 26.86 | 28.55 |
| | 24.76 | 25.75 | 29.39 | 31.81 |
| | 27.07 | 30.78 | 29.13 | 33.89 |
| | 31.41 | 36.82 | 28.28 | 38.52 |
| | 31.11 | 37.50 | 30.41 | 34.87 |
| | 32.29 | 38.09 | 29.00 | 35.68 |
| | 28.53 | 33.33 | | |
| ($\bar{x}$) | 28.64 | 33.16 | 29.92 | 33.63 |
| (SD) | 2.55 | 3.67 | 2.65 | 3.49 |
| (SE) | 0.08 | 1.16 | 0.88 | 1.16 |

| | R/L | | R/L |
|---|---|---|---|
| | 1.04 | | 1.08 |
| | 1.30 | | 0.94 |
| | 1.18 | | 1.05 |
| | 1.16 | | 1.06 |
| | 1.04 | | 1.08 |
| | 1.14 | | 1.16 |
| | 1.17 | | 1.36 |
| | 1.21 | | 1.15 |
| | 1.18 | | 1.23 |
| | 1.17 | | |
| ($\bar{x}$) | 1.16 | | 1.12 |
| (SD) | 0.08 | | 0.12 |
| (SE) | 0.02 | | 0.04 |
| | | 3.6% ↓ | |
| | | NS | |

Figure 5:
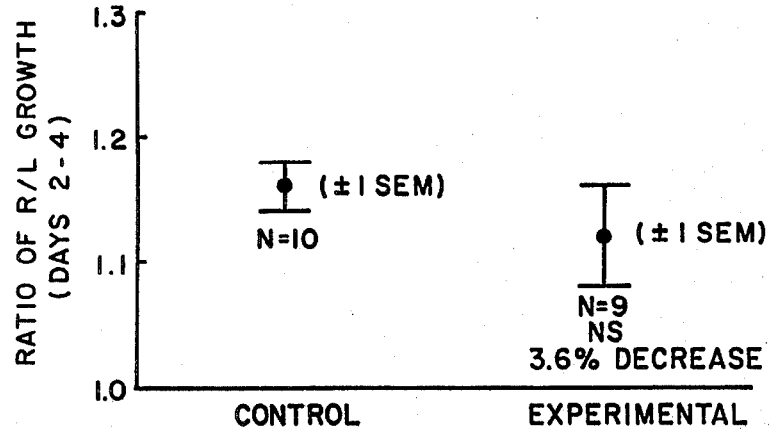

As shown in Table IV and FIG. 5, the group 4 animals (20.0 volts stimulation) experienced a 3.6% decrease in growth, from 1.16 average ratio R/L to 1.12 average ratio R/L. However, the results under group t-test analysis were not statistically significant. The correlation coefficients of weight gain and edema were 0.21 and 0.98 respectively.

Figure 6:
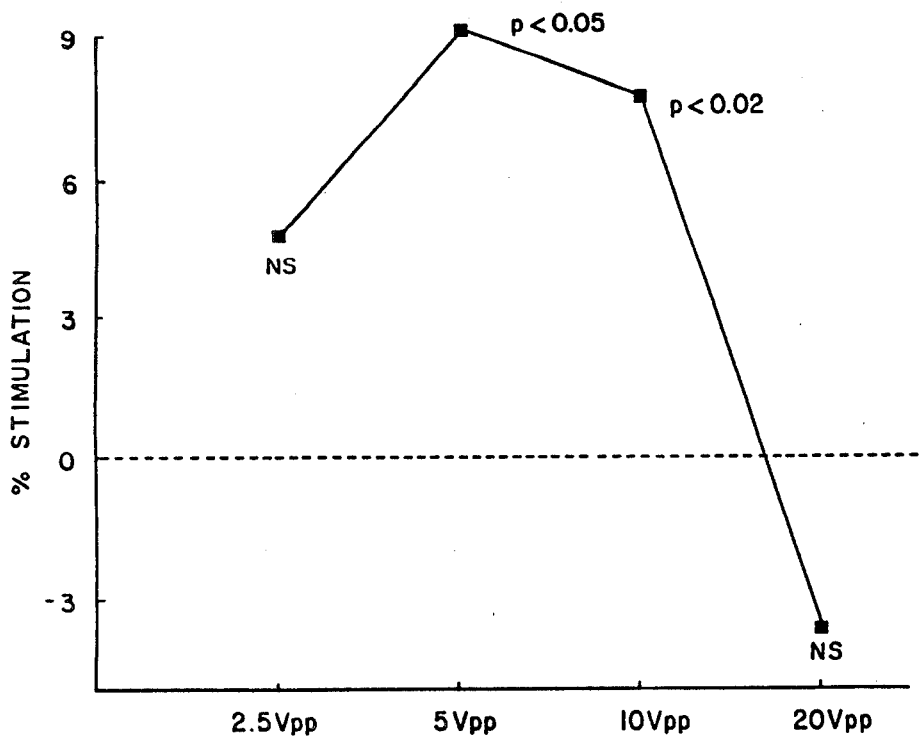
FIG. 6 is a typical dose-response curve showing the percentage increase in longitudinal growth for each of the four voltage stimulation signals.

FIG. 6 illustrates the dose-response curve for the effect of stimulating the proximal tibial growth plate in the in vivo rabbit. The vertical axis is the mean stimulated growth, in percent, of the stimulated tibiae in each group, using the unstimulated animals in that respective group as a base. The points plotted are 4.3% for the 2.5 volt group, 9.2% for the 5 volt group, 7.8% for the 10 volt group and −3.6% for the 20 volt group. A clear dose-response curve was obtained with the most growth experienced using a 5 volt signal. It appears that an optimal window of about 2.5 to 15 for the voltage parameter was obtained, above and below which either negative or insignificant results were experienced.

2. Second Analysis

While the results discussed above in the first data analysis were obtained by comparing the growth observed during the stimulation period (days 2–4) of the stimulated animals with the unstimulated or control animals during the stimulation period, in the second analysis the growth during the stimulated period (days 2–4) was compared to the growth during the unstimulated period (days 0–2) for only the stimulated animals in group 3, i.e. the 10 volt group.

Using a "paired t-test" the length change of days 0–2 was compared to that of days 2–4 and expressed as a ratio or percent difference. The double tetracycline label technique allowed the use of the unstimulated growth period (days 0–2) in each animal to serve as a control or base for the stimulated period (days 2–4) in that animal, thereby eliminating any error introduced by animal-to-animal variation.

However, the transverse oxytetracycline label which was deposited at day 0 was lost on many of the animals, because bone material which is about 96 hours old reaches the medullary canal (the hollow portion of the bone) and experiences remodelling to define this hollow canal. Therefore, only 3 animals in group 3 retained their transverse day 0 tetracycline label in both of their tibiae.

Figure 7:
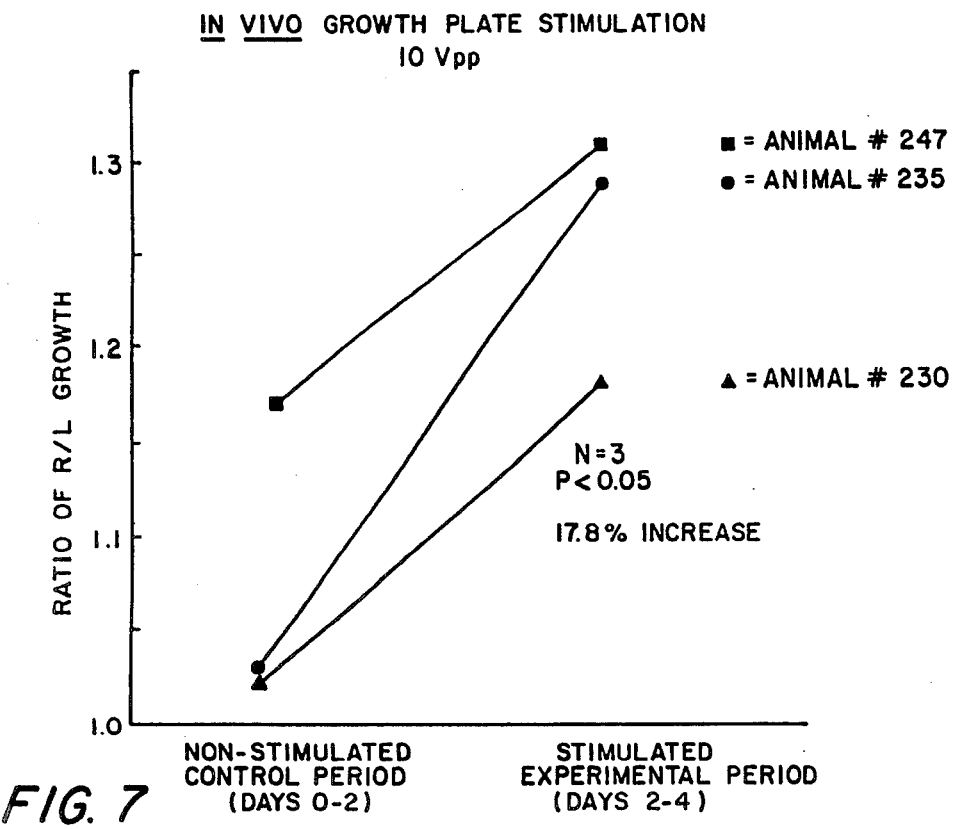
FIG. 7 illustrates typical bone growth results observed in three rabbits stimulated with 10 V peak-to-peak for two days relative to two days of non-stimulation.

As shown in FIG. 7, a mean 17.8% increase in length was seen (p 0.05, n=3, paired t-test) when the growth during the stimulation period (days 2–4) was compared to the growth during the nonstimulation period (days 0–2) in these three animals. Thus on the basis of this analysis alone a 10 volt peak-to-peak 60 KHz sine wave signal applied to electrodes in contact with the skin at appropriate positions relative to the epiphyseal growth plate was shown to induce epiphyseal plate growth in living beings.

The above experiments were actually carried out in four stages over a 6 month period, with one group in each stage. The 10 volt group, or group 3 was carried out first and generated the data for the second analysis as shown in FIG. 7. After it was determined that the first oxytetracycline line was lost in a large number of animals after 96 hours in the 10 volt group, the first oxytetracycline line was withheld for the 5.0 volt group, the 2.5 volt group and the 20 volt group which were carried out in the order just mentioned.

CONCLUSIONS

The results from both data analyses clearly show that longitudinal growth in bones can be accelerated by applying a continuous low voltage 60 KHz symmetrical sine wave signal of proper peak-to-peak amplitude via electrodes applied to appropriate positions relative to the epiphyseal growth plate of a bone.

Further, Tables I–IV show that there is no statistical difference between the left experimental legs and the left control legs, indicating that little if any distal stimulatory growth effect occurs in the left leg of an animal as a result of a stimulation signal applied to the right leg of that animal. In fact, the left legs in the experimental animals were shorter than the left legs in the control animals in the 2.5 volt, 5 volt and 10 volt groups. Therefore, it appears that epiphyseal growth plate stimulation can be limited to certain bones to at least a certain degree.

It is to be understood that the invention is not limited to the precise method shown and described, and no limitation is intended or should be inferred. It can be appreciated that numerous variations and modifications may be effected without departing from the true spirit and scope of the novel concept of the invention. It is of course intended to cover by the appended claims all such modifications as fall within the scope of the claims.

I claim:

1. A non-invasive method of stimulating growth in the epiphyseal plate in the bone of a living body comprising:

applying electrodes to the body of a subject in the vicinity of the epiphyseal growth plate of a bone; and supplying to said electrodes an alternating current stimulation signal in the ultrasonic frequency range of about 20 to 100 KHz for a sufficient period of time to effect an increase in the growth of said bone as compared with any bone growth that would occur naturally.

2. The method in accordance with claim 1 wherein the peak-to-peak voltage amplitude of the signal supplied to the electrodes is within the range of about 2.5 to 15 volts.

3. The method in accordance with claim 1 wherein the peak-to-peak voltage amplitude of the signal supplied to the electrodes is within the range of about 5 to 10 volts.

4. The method in accordance with claim 1 wherein the frequency of the signal supplied to the electrodes is about 60 KHz.

5. The method in accordance with claim 1 wherein the electrodes are bare metal electrodes in direct contact with the skin of the subject.

6. The method in accordance with claim 5 wherein a conductive gel is applied to the skin of the subject beneath the electrodes.

7. The method in accordance with claim 1 wherein the stimulation signal has a symmetrical sine waveform.

8. The method in accordance with claim 1 wherein the stimulation signal is applied to the body substantially continuously.

9. A non-invasive method of stimulating growth in the epiphyseal plate in the bone of a living body comprising:

applying two bare electrodes to the body of a subject in the vicinity of the epiphyseal growth plate of a bone; and supplying to said electrodes an alternating current stimulation signal having a generally symmetrical sine waveform with a voltage amplitude within the range of about 5 to 10 volts peak-to-peak and a frequency of about 60 KHz for a sufficient period of time to effect an increase in the growth of said bone as compared with any bone growth that would occur naturally.

* * * * *